United States Patent
Kramer

(10) Patent No.: US 11,224,508 B2
(45) Date of Patent: Jan. 18, 2022

(54) IMPLANTABLE TRANSCATHETER INTRACARDIAC DEVICES AND METHODS FOR TREATING INCOMPETENT ATRIOVENTRICULAR VALVES

(71) Applicant: George Kramer, Westbury, NY (US)

(72) Inventor: George Kramer, Westbury, NY (US)

( * ) Notice: Subject to any disclaimer, the term of this patent is extended or adjusted under 35 U.S.C. 154(b) by 100 days.

(21) Appl. No.: 16/543,480

(22) Filed: Aug. 16, 2019

(65) Prior Publication Data

US 2019/0365534 A1 Dec. 5, 2019

Related U.S. Application Data

(63) Continuation of application No. 14/994,881, filed on Jan. 13, 2016, now Pat. No. 10,383,726.

(60) Provisional application No. 62/103,018, filed on Jan. 13, 2015.

(51) Int. Cl.
*A61F 2/24* (2006.01)

(52) U.S. Cl.
CPC ............ *A61F 2/2418* (2013.01); *A61F 2/246* (2013.01); *A61F 2/2427* (2013.01); *A61F 2/2457* (2013.01); *A61F 2210/0004* (2013.01); *A61F 2250/0098* (2013.01)

(58) Field of Classification Search
CPC ............ A61F 2/2418; A61F 2220/0016; A61F 2/2466; A61F 2220/0008; A61F 2210/0014; A61F 2220/0075; A61F 2/2412; A61F 2/2427; A61F 2/2463; A61F 2250/0069; A61F 2220/0025; A61F 2210/0076; A61F 2/24; A61F 2/9522; A61F 2230/0093; A61F 2250/0007; A61F 2250/0037; A61F 2250/0048; A61F 2250/0051; A61F 2220/0066; A61F 2/848; A61F 2/246; A61F 2/2457; A61F 2210/0004; A61F 2250/0098
See application file for complete search history.

(56) References Cited

U.S. PATENT DOCUMENTS

| | | |
|---|---|---|
| 3,451,067 A | 6/1969 | Jordan |
| 7,837,727 B2 | 11/2010 | Goetz et al. |
| 8,092,525 B2 | 1/2012 | Eliasen et al. |
| 8,449,606 B2 | 5/2013 | Eliasen et al. |
| 2003/0049300 A1 | 3/2003 | Terry |
| 2005/0187616 A1* | 8/2005 | Realyvasquez ...... A61B 17/115 623/2.11 |
| 2006/0020332 A1 | 1/2006 | Lashinkski et al. |
| 2007/0072978 A1 | 3/2007 | Zoromski et al. |
| 2007/0093890 A1 | 4/2007 | Eliasen et al. |
| 2007/0265700 A1 | 11/2007 | Eliasen et al. |
| 2008/0288061 A1 | 11/2008 | Maurer et al. |
| 2010/0179649 A1 | 7/2010 | Richter et al. |
| 2011/0022164 A1 | 1/2011 | Quinn et al. |
| 2011/0077733 A1 | 3/2011 | Solem |

(Continued)

*Primary Examiner* — Ann Schillinger
(74) *Attorney, Agent, or Firm* — Daniel P. Burke & Associates, PLLC; Daniel P. Burke

(57) ABSTRACT

Heart valve implants and methods utilizing those valves designed to reduce or eliminate the regurgitant jet associated with an incompetent atrioventricular valve. The heart valve implants, which are deployed via a transcatheter venous approach, comprise a collapsible framework connected to an anchored guide shaft, a valve portion and an apron which permits ingrowth of native heart tissue into the apron.

16 Claims, 20 Drawing Sheets

(56) References Cited

U.S. PATENT DOCUMENTS

2012/0179244 A1 7/2012 Schankereli et al.
2015/0142101 A1* 5/2015 Coleman .......... A61B 17/12109
 623/2.11

* cited by examiner

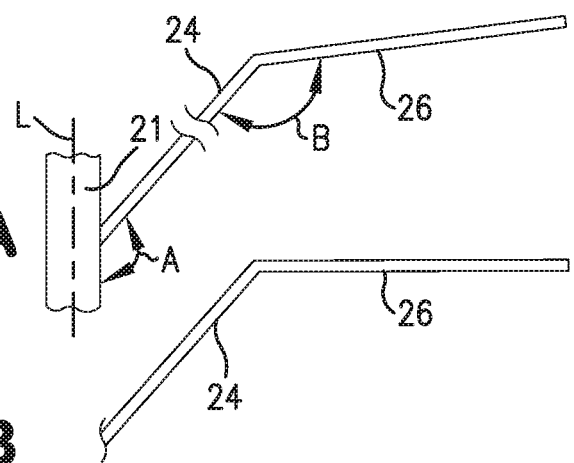
FIG. 16A
FIG. 16B
FIG. 16C
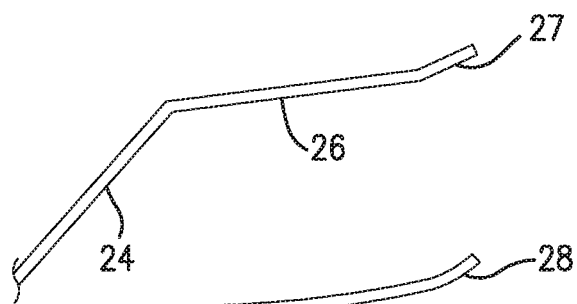
FIG. 17A
FIG. 17B
FIG. 17C

IMPLANTABLE TRANSCATHETER INTRACARDIAC DEVICES AND METHODS FOR TREATING INCOMPETENT ATRIOVENTRICULAR VALVES

RELATED APPLICATION DATA

This application is a continuation of U.S. patent application Ser. No. 14/994,881 filed on Jan. 13, 2016, which claims the benefit of Provisional Patent Application Ser. No. 62/103,018 filed on Jan. 13, 2015, which are hereby incorporated by reference.

Disclosed are heart valves and methods utilizing those valves designed to reduce or eliminate the regurgitant jet associated with an incompetent atrioventricular valve. The disclosed embodiments comprise valve devices and methods wherein, via a transcatheter venous approach, a collapsible frame is secured in a heart with an anchored guide shaft. The valve device is positioned so that it extends from a distal position in the ventricle to a more proximal position which is proximal to the leaflets of a native atrioventricular valve.

BACKGROUND

Some previously known methods of treating incompetent, i.e. leaking, atrioventricular valves comprise the steps of removing the patient's native valve leaflets and replacing them with an artificial valve. Some artificial valves, particularly those which are designed to be substantially stationery or fixed relative to the valve annulus, can create a substantial risk of stenosis or obstruction to the desired flow of blood into the ventricle.

SUMMARY

Disclosed valve devices include transcatheter intracardiac devices designed for placement within an incompetent native atrioventricular valve apparatus (i.e. mitral or tricuspid). The disclosed valve devices reduce or eliminate the regurgitant jet associated with the incompetent valve, without requiring removal of native valve structure. Thus, the disclosed devices are designed to cooperate with, rather than replace, native valve structure.

The valve devices comprise a valve connector, e.g. a tube, preferably formed of nitinol, braided nitinol wire or some similar material connected to a flexible guide shaft which preferably passes through the tubular connector. The flexible guide shaft comprises an active fixation distal end. For ease of reference, the valve connector is often referred to herein simply as the "tube" though valve connectors with other configurations can be utilized. The illustrated distal end is fixed into position in the ventricular apex or ventricular wall with an active fixation corkscrew. In preferred embodiments, a nitinol tube can be secured at a plurality of different positions on the flexible guide shaft thereby permitting adjustment of the overall length of the device and consequently adjustment of the placement of the operable valve portion relative to the native heart valve.

A framework is connected to the valve connector. In one embodiment, the proximal end of a nitinol tube is formed, braided or cut, e.g. laser cut, to create a plurality of angled fingers which serve as the framework. Each finger of the illustrated embodiments has an inner or center portion which is angled radially outwardly relative to the tubular distal portion and an outer portion which is angled further radially outwardly than the inner portion. Alternative embodiments comprise additional structure, e.g. branches, between the inner portions of the fingers. The framework thus extends radially outwardly from the tubular portion and is designed to prevent the prolapse or flair of the artificial valve portion and the native valve leaflets.

A valve portion is located proximate and distally of the inner portions of the fingers forming the framework. The valve portion can comprise artificial valve leaflets attached to the distal or outer side of the inner portions of the framework and positioned so that the artificial valve leaflets are prevented from prolapsing by the inner portion of the framework. The valve portion is preferably formed in a generally tubular shape. Preferred embodiments comprises an artificial valve portion in the form of a collapsible tube. The collapsible tube can be formed with or without leaflets. The valve portion is formed of suitable materials, such as ePTFE made by W.L. Gore & Associates, Inc., porcine pericardium or processed small intestine submucosa. A proximal section of the valve portion is attached to the framework and forms the one-way valve. An apron is attached to the distal or outer side of the framework proximate the outer portions of the fingers.

The valve controls the one-way flow of blood from the atria into the ventricle. The valve closes by collapsing on itself due to pressure differentials created during the systolic portion of the cardiac cycle and is assisted by the motion of the native leaflets. The relative positions of the fingers of the framework and the artificial valve portion prevent the native valve leaflets and the artificial valve portion from prolapsing into the atria.

The disclosed artificial valves are preferably placed via a transcatheter venous approach wherein the valve is collapsed within a catheter, positioned within a heart, and the guide shaft is secured to the ventricular apex or ventricular wall.

During placement, the length of the valve device can be adjusted by adjusting the position of the tube relative to the guide shaft in order to facilitate optimal placement of the valve device in the heart. Preferably, after placement the artificial valve portion, e.g. artificial leaflets, is positioned within the native valve. As used herein, the phrase "within" when used with reference to a native heart valve or native leaflets indicates that the artificial valve portion is positioned between the native leaflets. The valve portion is closed by the normal movement of the native leaflets during systole resulting in a reduction or elimination of the regurgitant jet. The apron, which extends over and is in contact with the atrial annulus, serves as a platform for native tissue ingrowth. As native tissue grows into the apron, the proximal end of the valve device is permanently fixed within the atrium.

One method comprises the steps of positioning one of the valve devices within a patient's heart via a transcatheter venous procedure and anchoring the device to a heart wall. Some methods also comprise the step of adjusting the position of the tube relative to the guide shaft in order to properly position the valve portion and apron for optimal sealing and blood flow. A preferred adjustment step comprises observing the valve device while in a heart via fluoroscopy and transesophageal echocardiography, removing the heart device from the patient, adjusting the relative positions of the guide shaft and tube, and repositioning the device in the heart. In alternative methods, the position of the tube relative to the guide shaft is changed while the device is in the patient's body.

BRIEF DESCRIPTION OF THE DRAWINGS

FIGS. 16A-16C illustrate alternative orientations of the outer portions of fingers of the framework.

FIGS. 17A-17C illustrate alternative configurations for outer tips of fingers of frameworks of the present invention.

DETAILED DESCRIPTION

FIGS. 1-6 illustrate one embodiment of the present invention which comprises an anchoring guide shaft 10, a tube 20 which forms a valve connector, an apron 30 and a valve portion 40.

Figure 18:
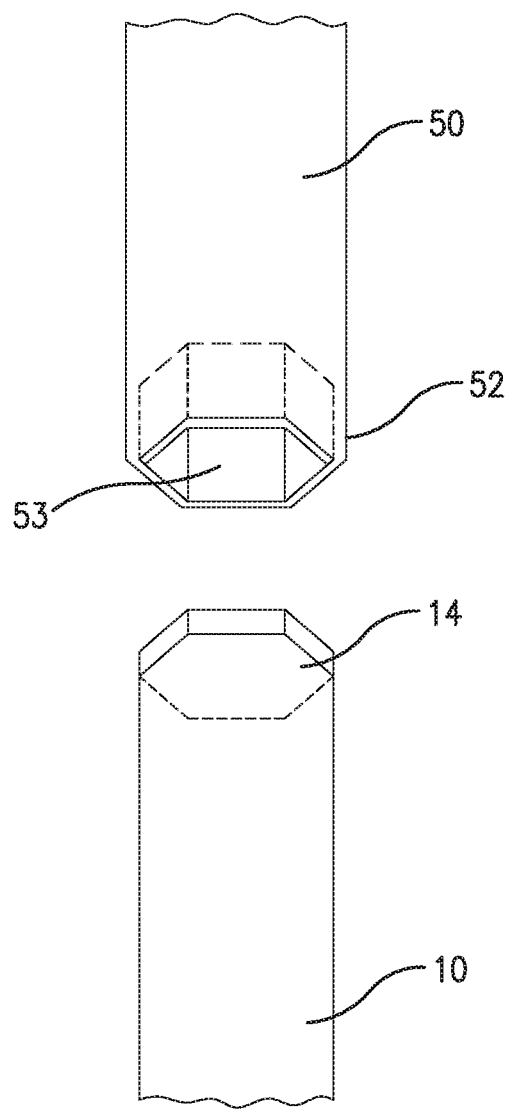
FIG. 18 is a partial, cross-sectional view of a detachable anchoring tool and a flexible shaft of one embodiment.
Figure 19:
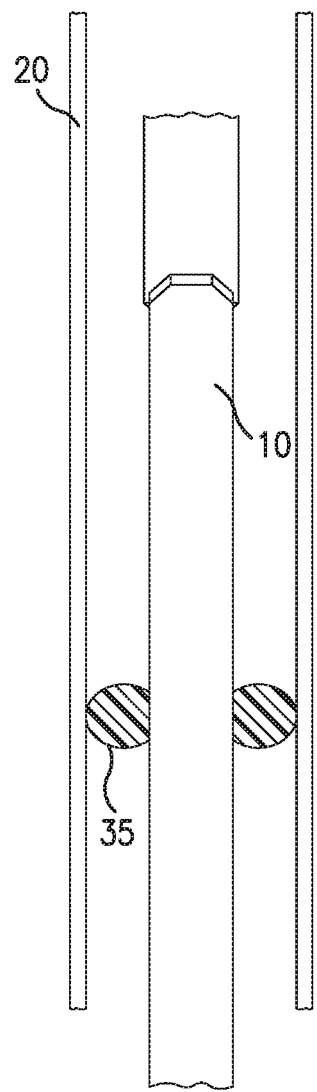
FIG. 19 is a partial, cross-sectional view illustrating an adjustment mechanism for adjusting the relative positions of a flexible guide shaft and tube of one embodiment.
Figure 20:
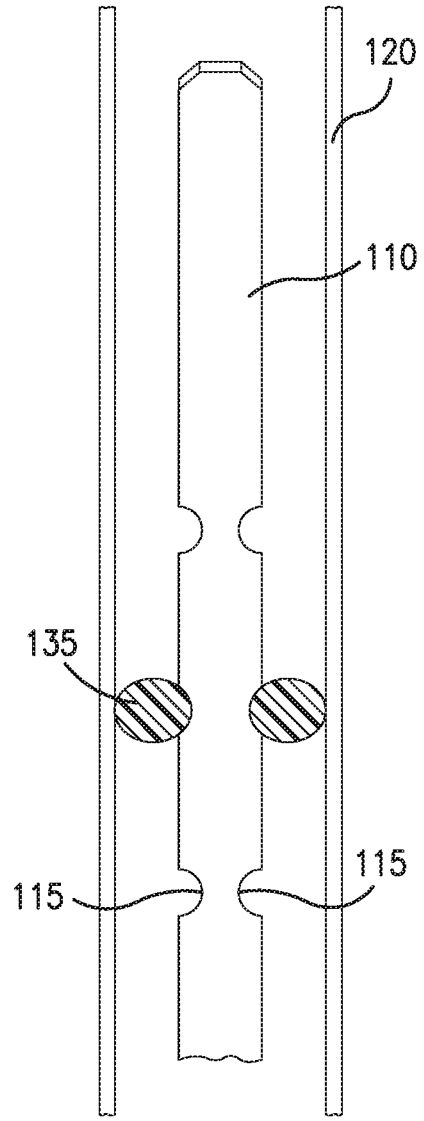
FIG. 20 is a partial, cross-sectional view illustrating an adjustment mechanism for adjusting the relative positions of a flexible guide shaft and tube of another embodiment.

Guide shaft 10 can be formed of a flexible polyurethane in the same manner as is common with pacemaker lead wires. Suitable materials include Elasthane™ 55D Thermoplastic Polyether Polyurethane (TPU) sold by DSM Biomedical of Exton, Pa., Silicone 4719 sold by Medtronic, a silicone-polyurethane co-polymer such as those sold by St. Jude Medical, and other materials. Guide shaft 10 comprises an active fixation anchor in the form of a corkscrew 12 at the distal end thereof. The illustrated corkscrew is adapted to be secured to a heart wall by rotating the internal portion of the shaft during transcatheter placement. FIGS. 18-20 show an exemplary proximal end 14 of guide shaft 10 which is designed to be releasably engage by the distal end 52 of a placement shaft 50. As best shown in FIG. 18, in this embodiment proximal end 14 of guide shaft 10 is generally hexagonally shaped and distal end 52 of placement shaft 50 has a hexagonal recess 53 adapted to releasably engage proximal end 14. During placement of the fixation anchor 12, placement shaft 50 extends through tube 20 and engages the proximal end 14 of flexible guide shaft 10. The proximal end (not shown) of placement shaft 50 extends out the proximal end of a delivery catheter (not shown) and can be rotated. Rotation of the placement shaft 50 rotates guide shaft 10 thereby causing the corkscrew to burrow into the desired site of the ventricular apex or ventricular wall.

With reference again to FIGS. 1-6, tube 20 is preferably formed of braided nitinol wire, nitinol, or some similar resilient biocompatible material, which can be treated to have the desired shape-memory after it exits a catheter. The illustrated tube 20 is formed of braided nitinol wire. Valve connectors preferably have a length of about 0.5-4 cm and a width of about 5-8 Fr. When the valve connector is tubular, the width is the external diameter of the tube. Tubular valve connectors preferably have a diameter not greater than 8 Fr., and most preferably not greater than 6 Fr.

In this illustrated embodiment, the valve connector is a tube 20 which receives the flexible guide shaft 10 and through which passes a placement shaft. Tube 20 comprises at least one attachment point for securing the tube 20 to the guide shaft 10. As explained in greater detail below, in preferred embodiments, the position of the tube 20 relative to the guide shaft 10 can be adjusted in order to facilitate optimal placement of the valve device in a heart.

Figure 3:
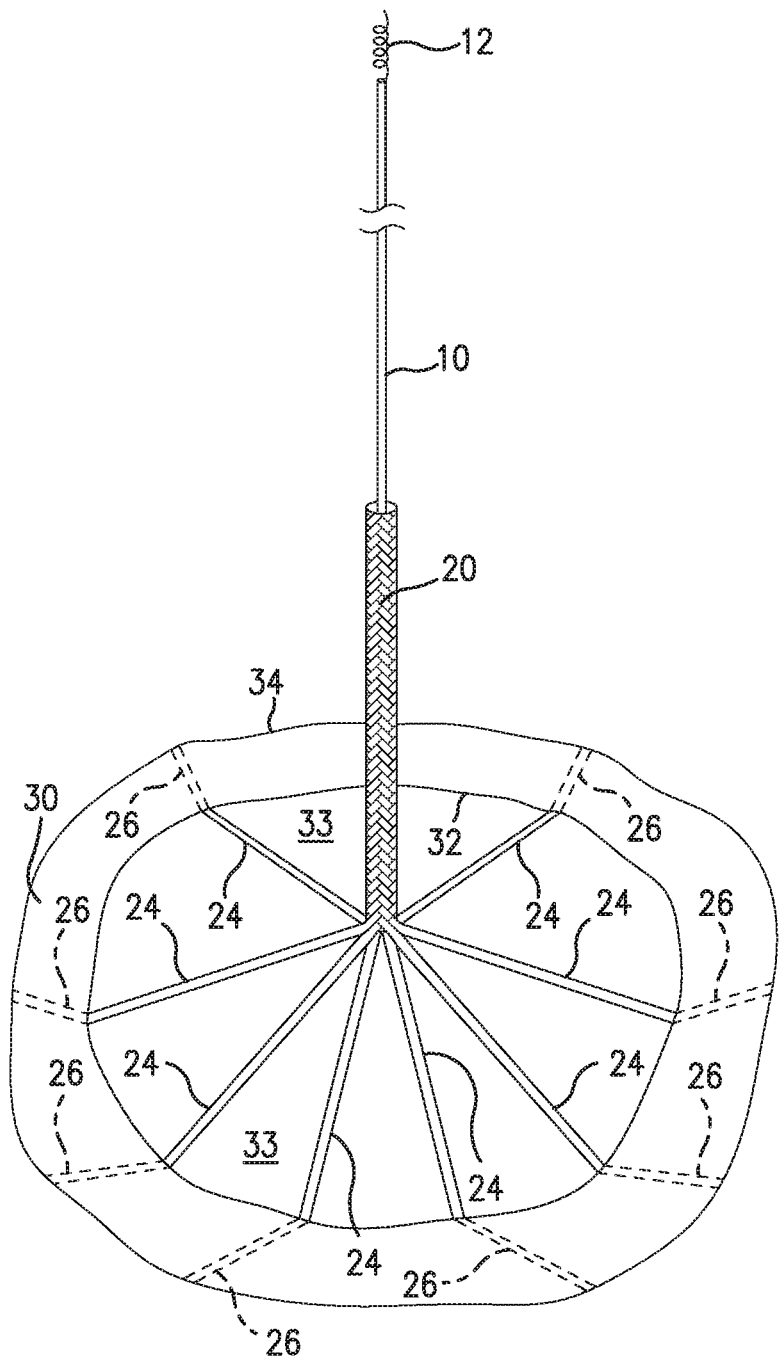
FIG. 3 is a bottom perspective view of the guide shaft, tube and apron of the embodiment shown in FIG. 1
Figure 5:
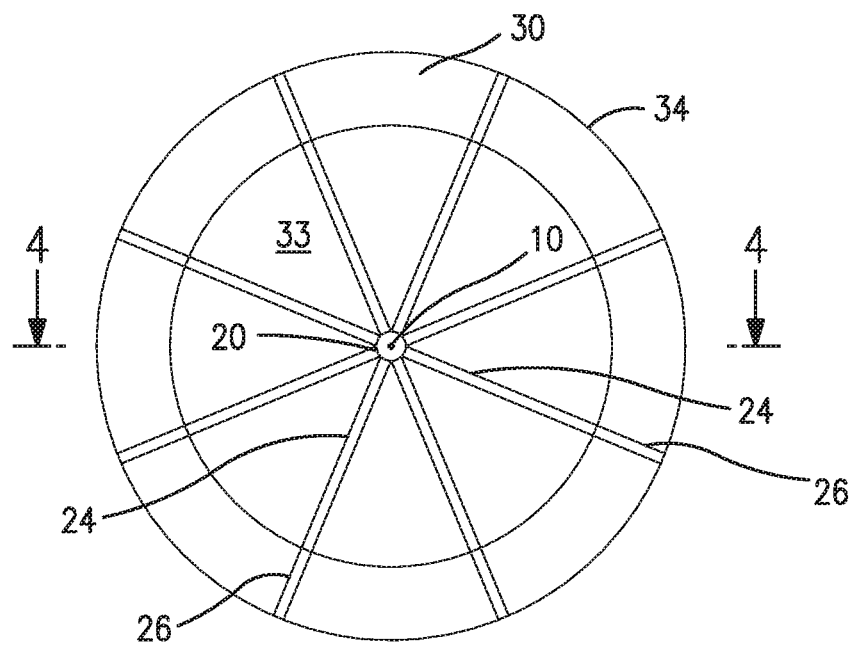
FIG. 5 is a top view of the guide shaft, tube, framework and apron of the embodiment shown in FIG. 1.
Figure 4:
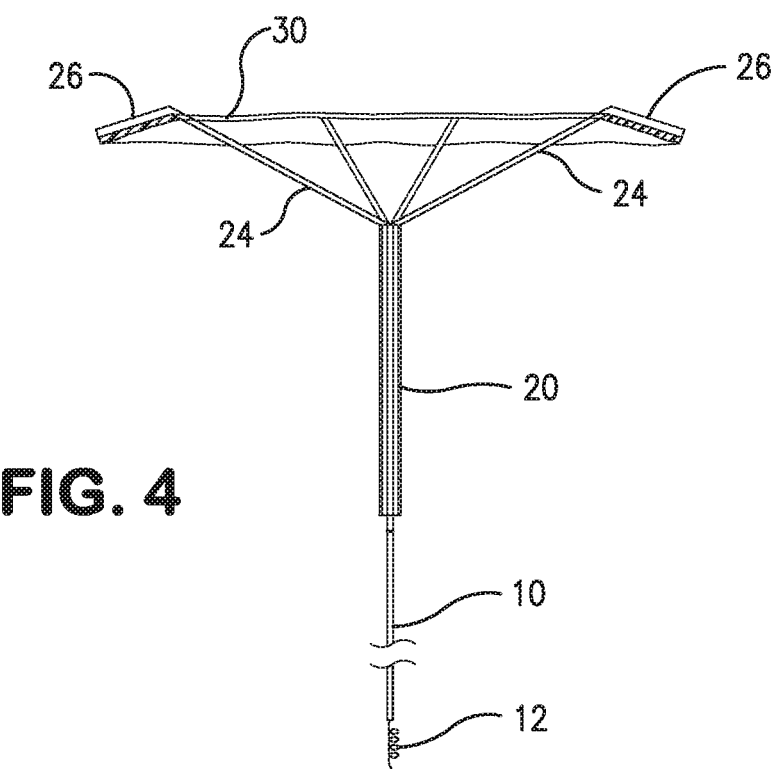
FIG. 4 is a cross-sectional side view taken along line 4-4 of FIG. 5.
Figure 6:
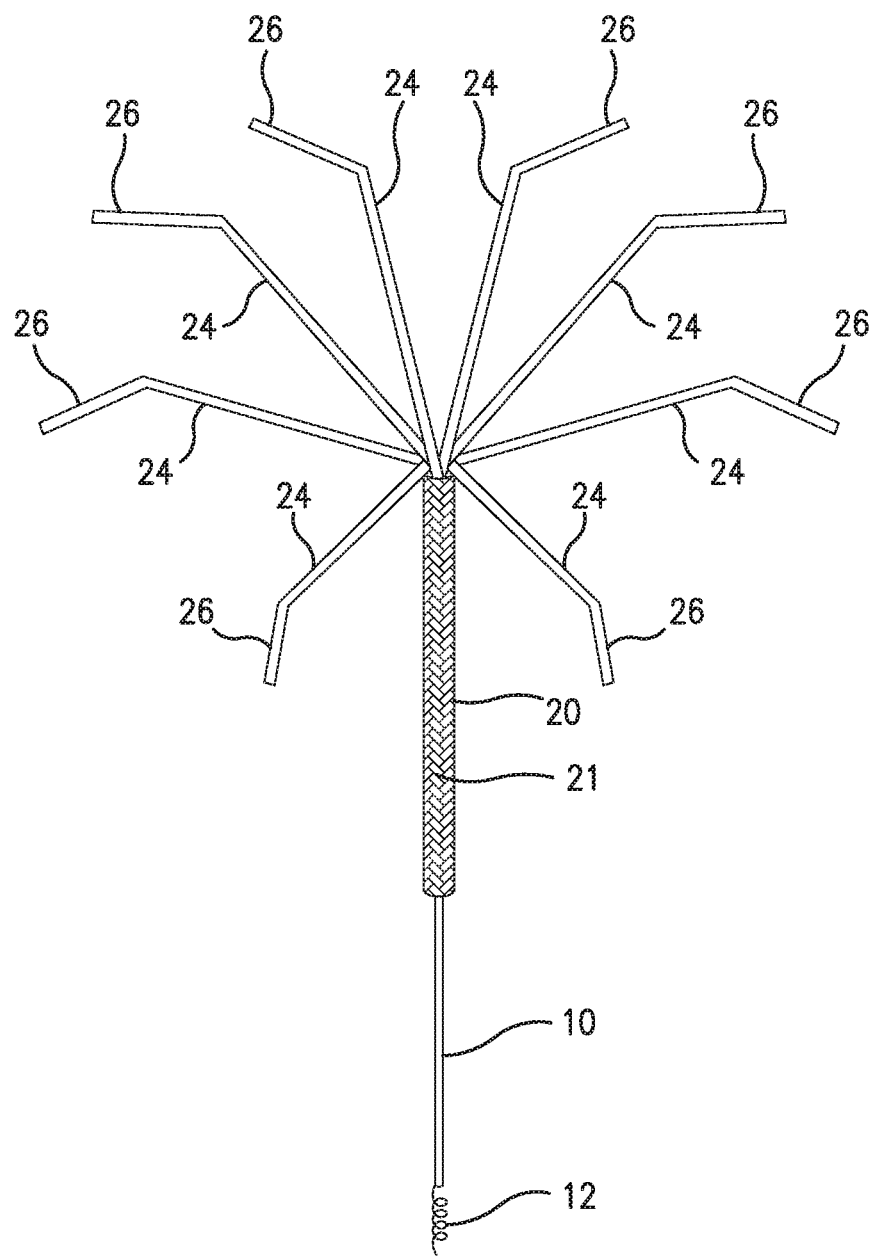
FIG. 6 is an upper perspective view of the guide shaft, tube and framework of the embodiment shown in FIG. 1.
Figure 7A:
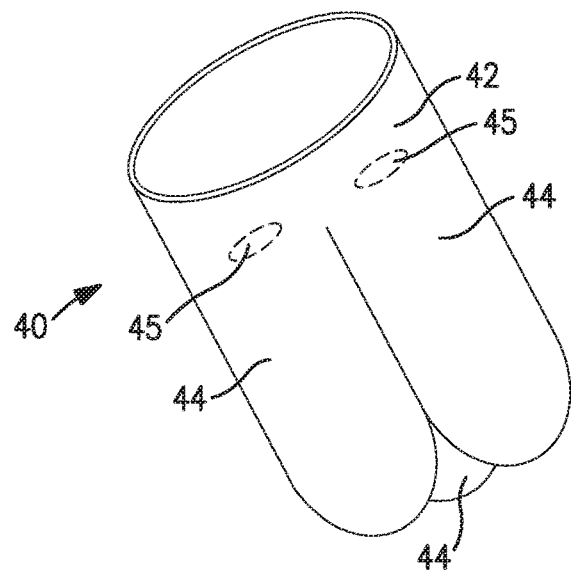
FIGS. 7A-7E are perspective views of five alternative valve portions.
Figure 7B:
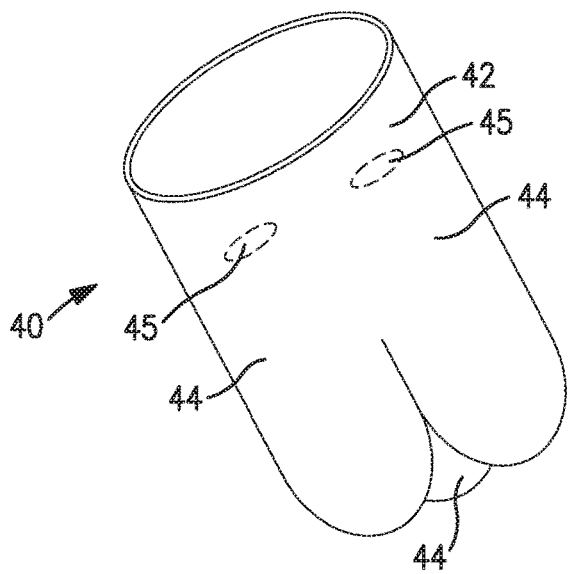
Figure 7C:
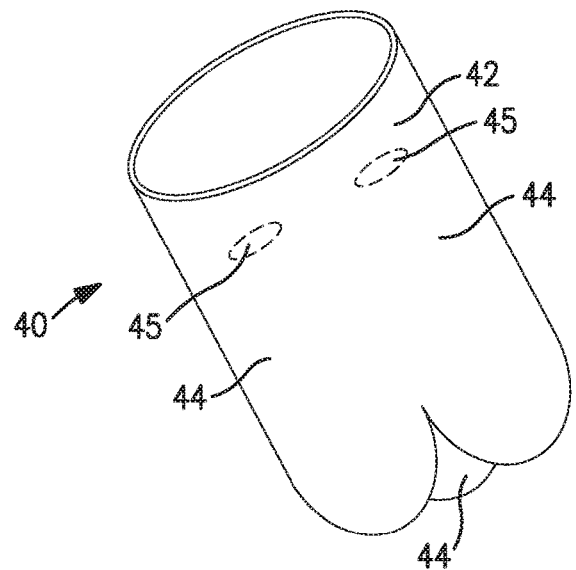
Figure 7D:
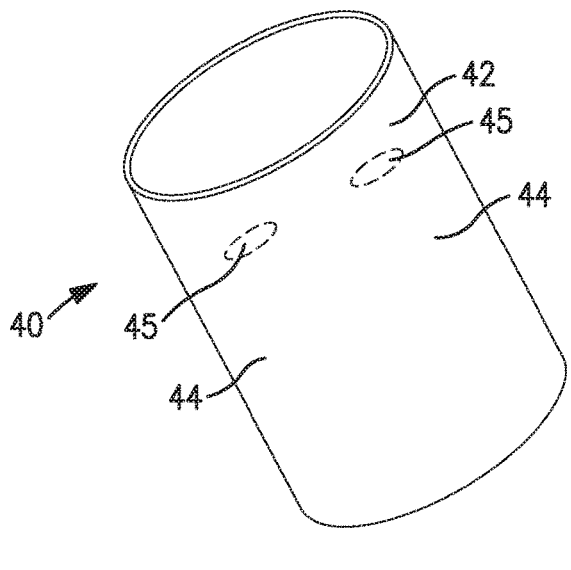
Figure 7E:
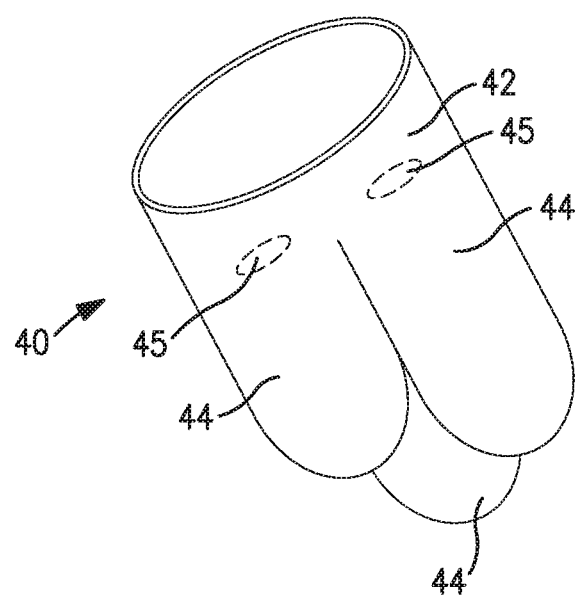

A framework is provided proximate the proximal end of the tube. The proximal end of the tube can be formed, braided or cut, e.g. laser cut, to create a plurality of splayed, angled fingers that serve as a framework which is integrally formed with the tube. As best shown in FIG. 3, in this illustrated embodiment, the fingers of the framework are preferably formed of the same strands which form the tube 20. Each finger 22 has a center portion 24 which is angled radially outwardly relative to the tube 20 and an outer portion 26 which is angled further radially outwardly than the inner portion 24. Thus, this illustrated embodiment comprises fingers 22 formed with two predetermined bends, i.e. one bend at the junction of the tube 20 and inner portion 24, and a second bend at the junction of the inner portion 24 and the outer portion 26. Alternative designs can have a greater number of bends in the fingers 22. Frameworks preferably comprise at least eight fingers and can have more fingers, e.g. twelve or sixteen. The fingers each preferably have a length of about 1-2.5 cm. While the preferred frameworks comprise fingers shaped with a plurality of linear sections disposed at angles (other than) 180° to each other, and with or without intermediate bridging structure, alternative and less preferred frameworks (not shown) are formed with curved fingers. Such curved fingers are preferably shaped to conform to the curvature of the native leaflets.

Atrial apron 30 is secured to the distal portions 26 of the fingers 22. Atrial apron 30 is preferably sutured onto the outside or distal side of fingers 22. For purposes of reference, in FIGS. 2-3, apron 30 is deemed secured to the lower side, i.e. the distal side, of the outer portions 26 of fingers 22. The apron 30 is generally donut-shaped, i.e. comprising a central opening 33 defined by inner edge 32. Apron 30 also has an outer edge 34. The central opening 33 defined by inner edge 32 allows for blood flow. Apron 30 is formed of a thin, material which is non-porous to blood in the heart environment. The apron 30 can be formed, for example, of ePTFE, porcine tissue, bovine tissue and canine tissue. Such tissue may comprise processed small intestine submucosa or processed pericardium.

The apron 30 is designed to be positioned on the floor of the atrium and serves as a platform for native tissue ingrowth. As native tissue grows into the apron 30, the proximal end of the valve device becomes permanently fixed within the atrium.

With reference to FIGS. 1, 2 and 7A-7E, the devices of the present invention also comprise an artificial valve portion 40 disposed proximate to and distally of the inner portions 24 of fingers 22. Valve portion 40 is designed to open fully so as not to impede the flow of blood during the diastolic phase of the heart cycle and to be closed by the native heart valve leaflets during the systolic phase when the artificial valve portion 40 is urged upwardly. The artificial valve portion 40 is prevented from prolapsing by inner portions 24 of fingers 22.

The artificial valve portion 40 can have different forms. FIGS. 7A-7E are perspective views of exemplary valve portions 40 of different embodiments. The valve portion 40 shown in FIG. 4 A comprises a ring portion 42 and a plurality of leaflets 44. Leaflets 44 are preferably integrally formed with ring portion 42. This valve portion comprises three leaflets 44, but it is also possible to use a valve portion comprising a different number of leaflets, e.g. two. The valve portion 40 shown in FIG. 7B comprises shorter, scallop-shaped leaflets. In other words, the slits in the valve portion shown in FIG. 7B which extends proximally from the distal end of the valve portion do not extend as far proximally as the slits in the valve portion shown in FIG. 7A. The valve portion shown in FIG. 7C has scallop-shaped distal edges, but does not have slits extending proximally from the distal scalloped edges. The valve portion shown in FIG. 7D has a generally tubular shape with a straight circumferential distal edge, i.e. without individual leaflets. The valve portion shown in FIG. 7E has three leaflets 44 of different lengths, each with scallop-shaped distal edges. The leaflets 44 of the valve portion shown in FIG. 7E extend distally different distances from the ring portion 42.

Figure 1:
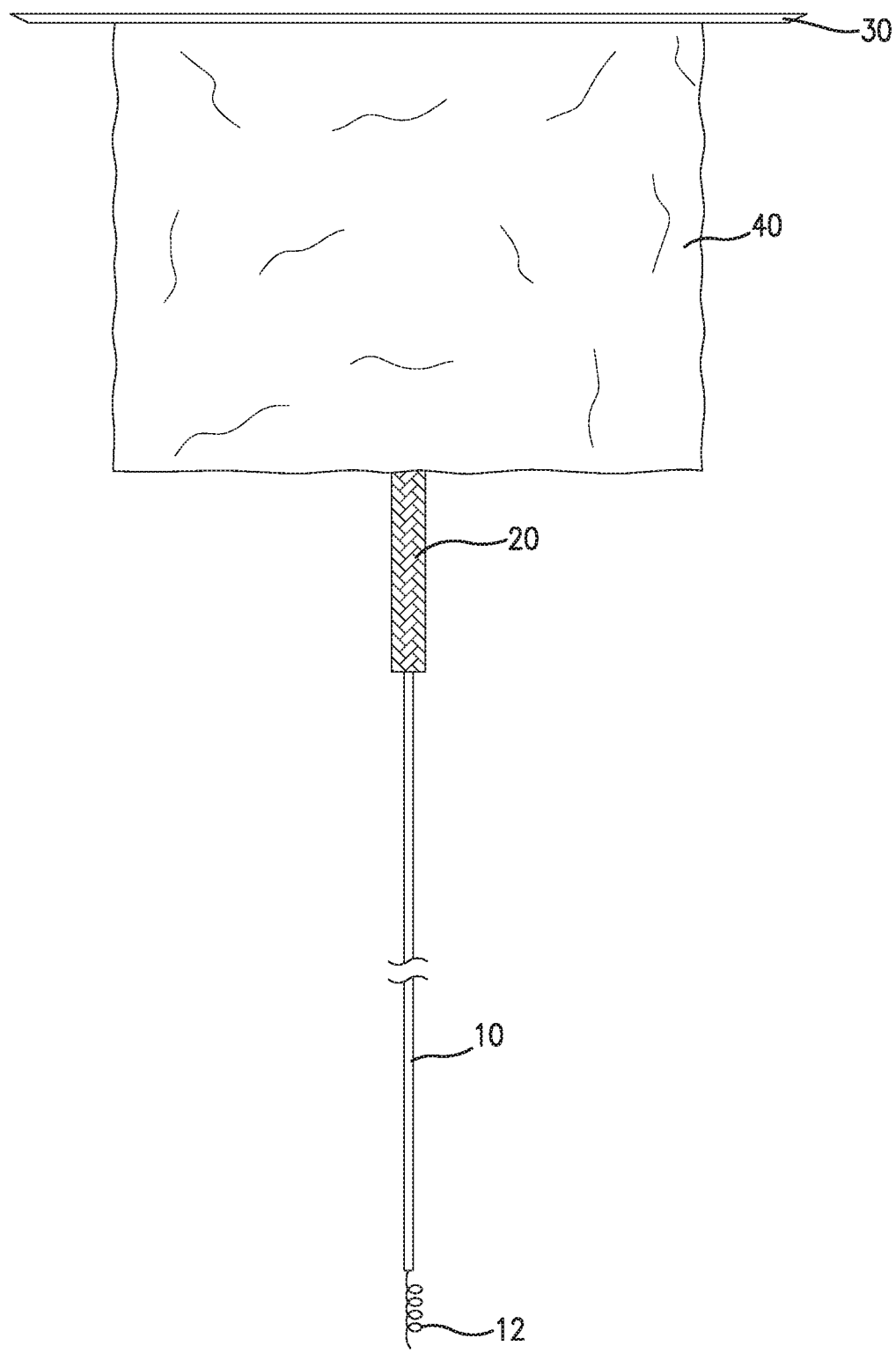
FIG. 1 is a side view of one embodiment of the present invention with the valve portion in the open (diastole phase) position.
Figure 2:
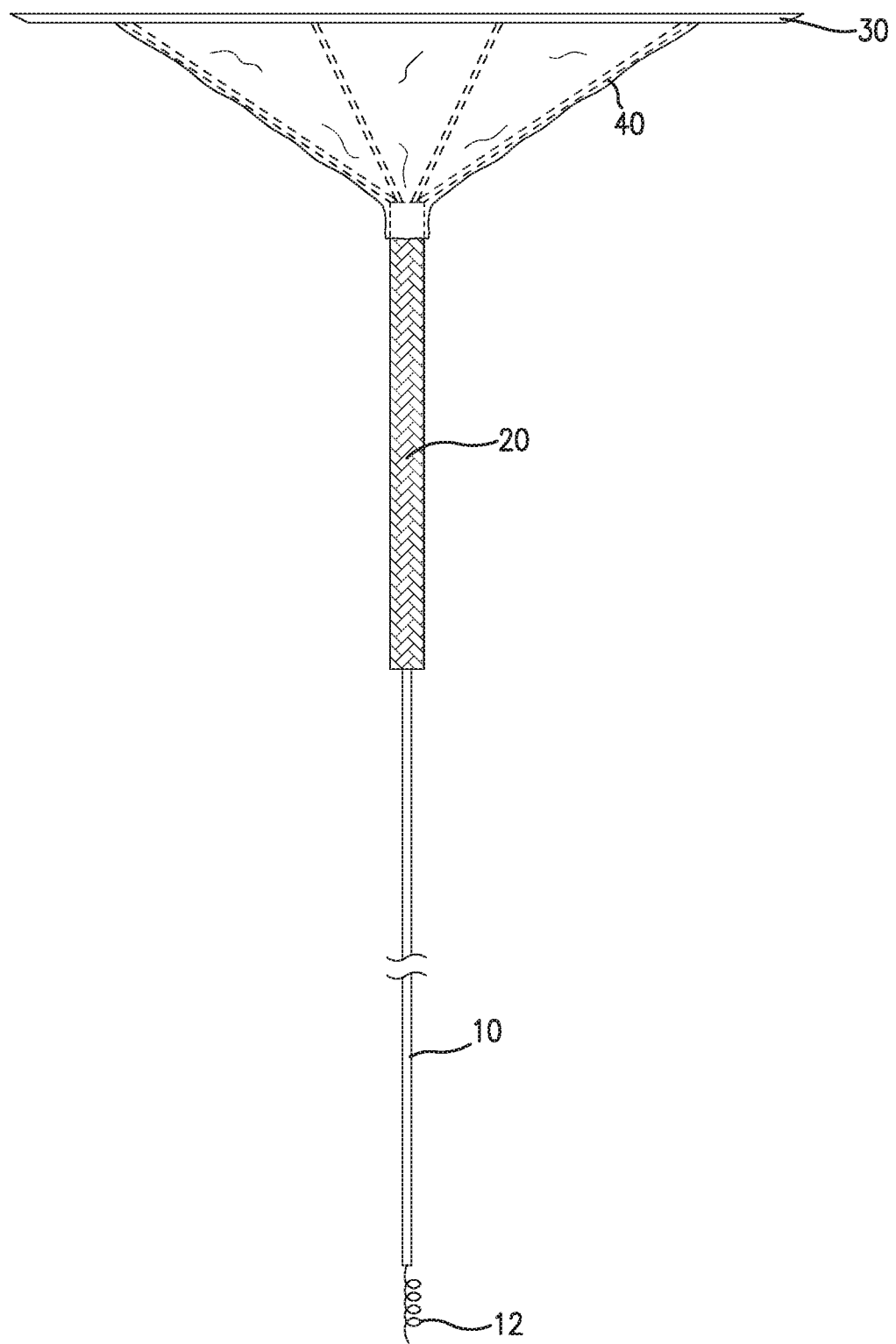
FIG. 2 is a side view of the embodiment of FIG. 1 with the valve portion in the closed (systole phase) position.
Figure 8:
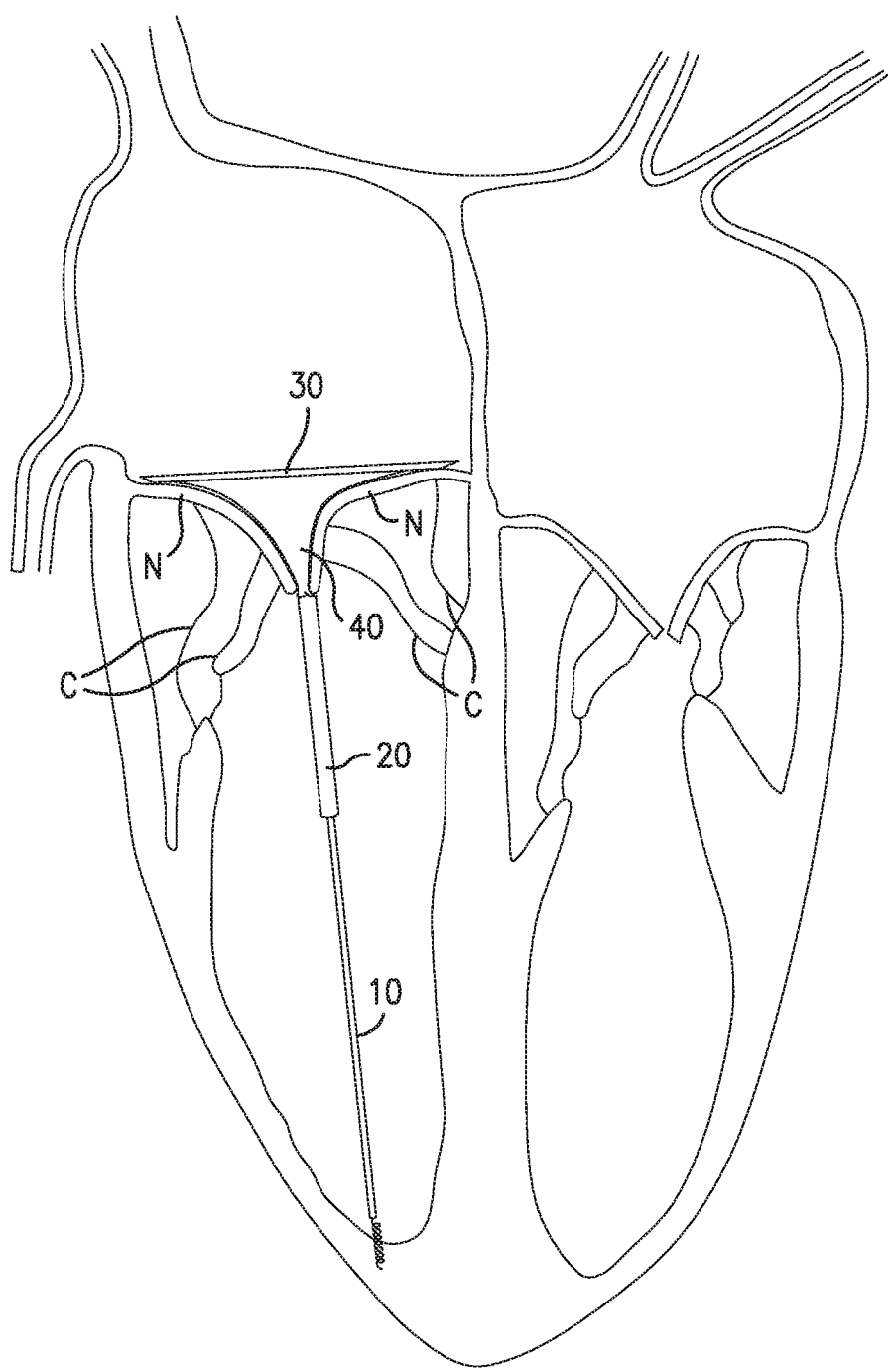
FIG. 8 illustrates a valve device shown in FIG. 1 installed in a tricuspid valve during the systolic portion of the cardiac cycle with the valve portion closed.

Ring portion 42 is secured, e.g. sown or glued, to the distal portion of apron 30 proximate inner edge 32 and preferably also to proximal portions of inner portions 24 of fingers 22. Leaflets 44 open during the diastolic portion of the cardiac cycle to minimize the obstruction of blood flowing into the ventricle. During the systolic portion of the cardiac cycle, leaflets are urged proximally but are prevented from prolapsing into the atria by the inner portions 24 of fingers 22 as shown in FIGS. 2 and 8. Thus, during systole, the resilient artificial valve portion is in contact with the framework. The design of leaflets 44 and their positioning relative to inner portions 24 of fingers 22 reduces or eliminates the regurgitant jet associated with an incompetent atrioventricular valve.

Valve portion 40 can be formed of ePTFE, porcine tissue, bovine tissue or canine tissue. Such tissue may be processed small intestine submucosa or processed pericardium. The valve devices are intended for use in humans and other mammals. While the combined apron 30 and fingers 22, e.g. nitinol fingers, have some flexibility, they are not as flexible as the artificial leaflets 44 of valve portion 40. All components are formed of suitable biocompatible materials.

Valve portion 40 also preferably comprises markers 45, e.g. radio dense implants or markers, preferably disposed in the ring portion 42 slightly proximally of the proximal end of the leaflets 44, but alternatively in other positions, to permit a surgeon to observe the valve's position via fluoroscopy and transesophageal echocardiography during and after surgery.

The entire valve device comprising the guide shaft 10, tube 20, framework, apron 30 and valve portion 40 are fully collapsible for placement via a transcatheter venous procedure.

The tube 20 can be fixed in one position on shaft 10 or can be selectively repositionable in different positions on the flexible shaft 10 thereby making the overall length of the device adjustable and consequently facilitating the desired placement of the operable valve portion. In the preferred illustrated arrangement, the tube 20, which preferably has greater rigidity than guide shaft 10, does not extend to the distal end of the shaft 10. By spacing the distal end of tube 20 from the heart wall, the risk of damage, e.g. puncturing, to the ventricle is reduced.

Figure 9:
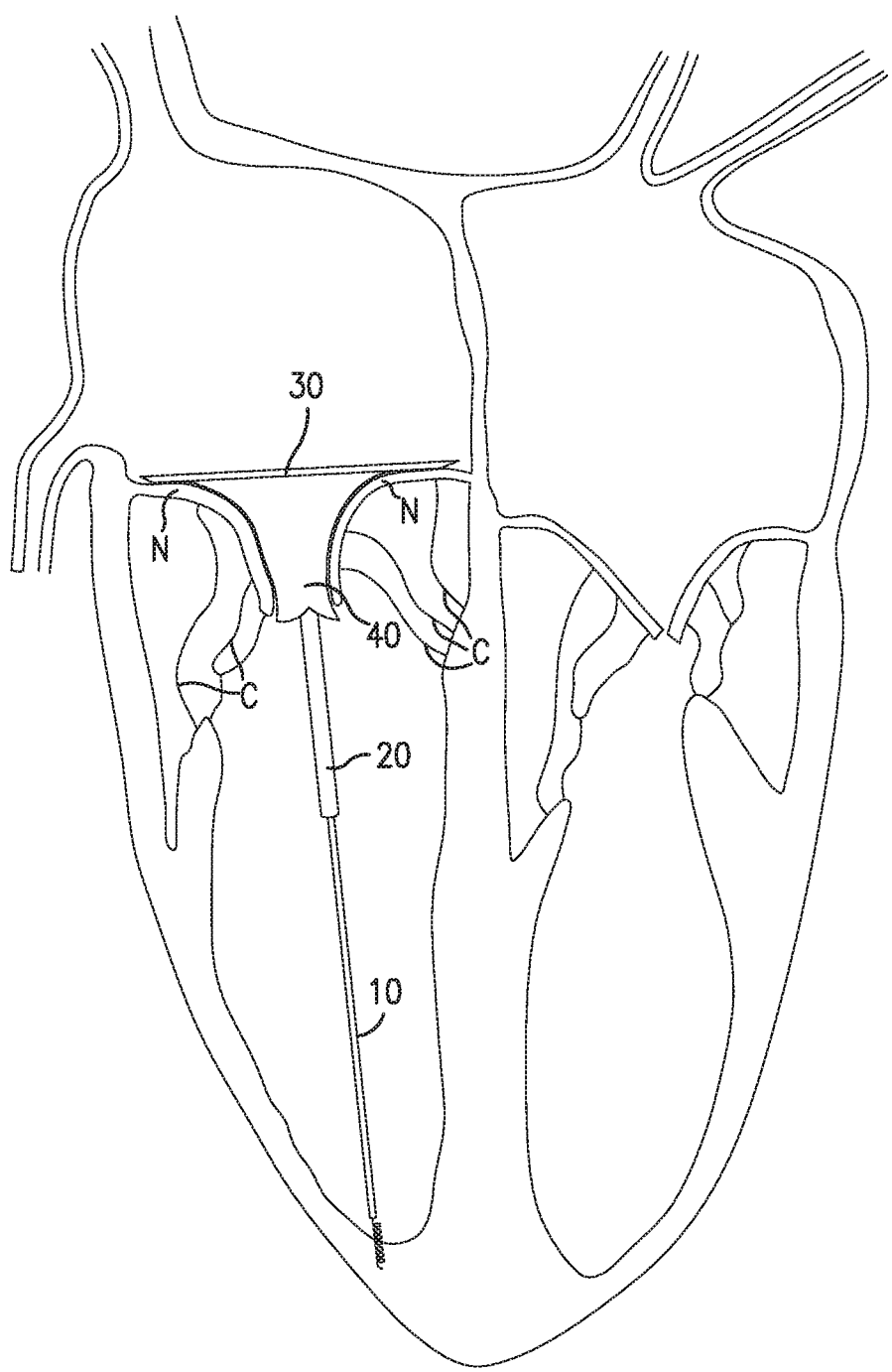
FIG. 9 illustrates a valve device of FIG. 1 installed in a tricuspid valve during the beginning of the diastolic portion of the cardiac cycle with the valve portion partially open.
Figure 10:
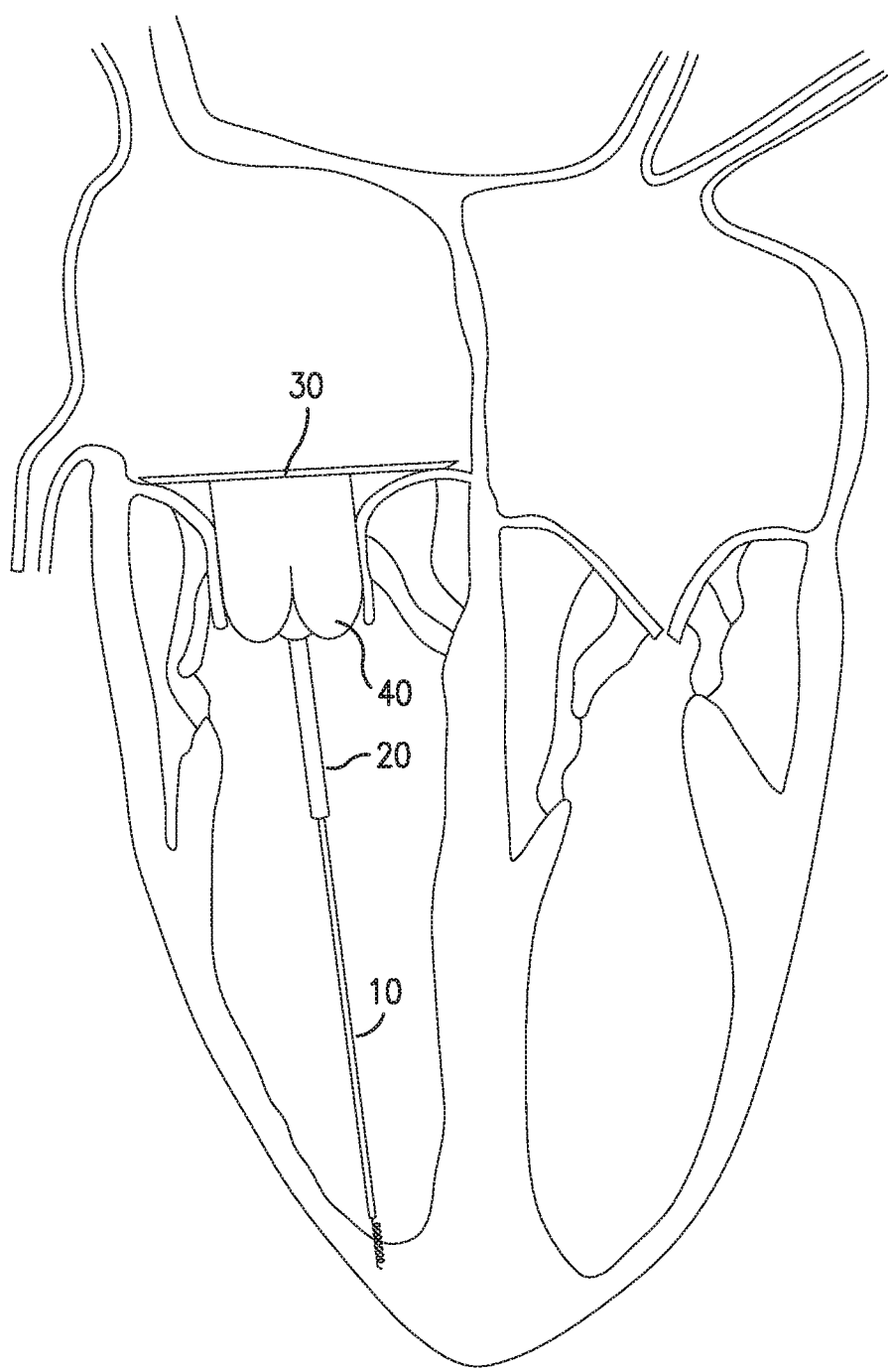
FIG. 10 illustrates a valve device shown in FIG. 1 installed in a tricuspid valve during the diastolic portion of the cardiac cycle with the valve portion fully open.
Figure 11:
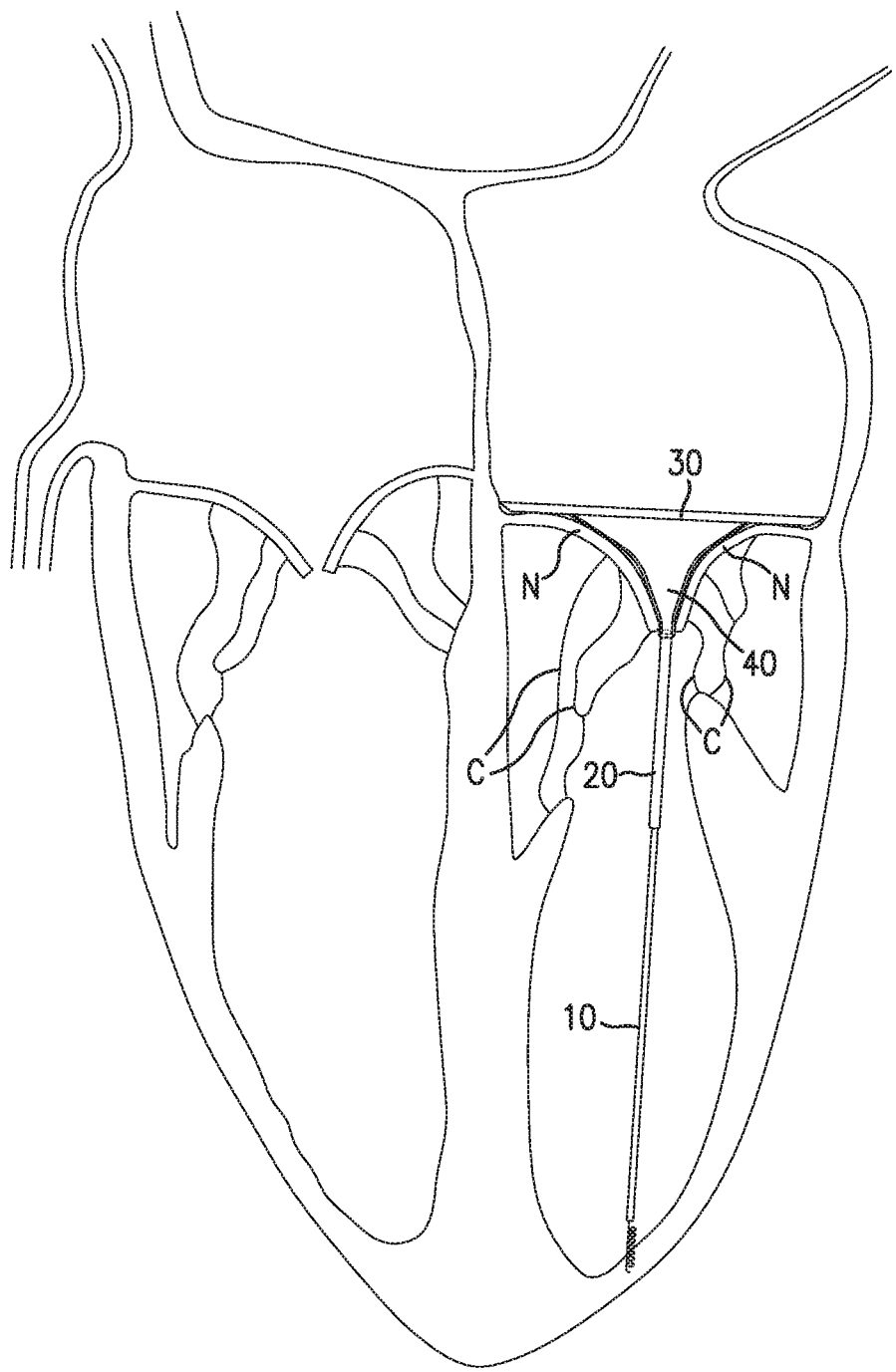
FIG. 11 illustrates the valve device of FIG. 1 installed in a mitral valve with the valve portion closed.

FIGS. 8-11 illustrate valve devices shown installed in heart with FIGS. 8-10 showing a valve device in a tricuspid valve during different times in a heart cycle and FIG. 11 shows a valve device installed in a mitral valve. These figures depict native valve leaflets N and chordae tendineae C.

FIG. 8 illustrates a valve device of the present invention installed in a tricuspid valve during the systolic portion of the cardiac cycle with the valve fully closed. As indicated, the native valve leaflets N have closed the artificial valve portion 40 to form a tight seal around tube 20. FIG. 9 illustrates a valve device of the present invention installed in a tricuspid valve during the beginning of the diastolic portion of the cardiac cycle with the valve portion 40 partially open. FIG. 10 illustrates a valve device of the present invention installed in a tricuspid valve during the diastolic portion of the cardiac cycle with the valve portion 40 and the native leaflets N fully open. As illustrated in FIGS. 8-10, the apron 30 is positioned over a proximal portion of the native leaflets and extends outwardly toward the valve annulus. FIG. 11 illustrates a valve device of the present invention installed in a mitral valve during the ventricular systolic portion of the cardiac cycle with the valve fully closed. As indicated, the native valve leaflets N have closed the artificial valve portion 40 to form a tight seal around tube 20.

During surgery, the collapsed valve device comprising collapsed fingers, apron and valving portion as well as guide shaft 10 and tube 20, is inserted through a catheter and observed relative to the native heart structure via fluoroscopy and transesophageal echocardiography. If the artificial leaflets are not properly aligned with the native leaflets, the valve device can be removed from the patient and the tube 20 repositioned relative to the guide shaft 10. This adjusting step is repeated until desired alignment is achieved, preferably with the device positioned so that apron 30 is on the floor of the atrium to minimize risk of paravalvular leaks. This adjustment step can also be performed in vivo. When a valve device of the present invention is going to be installed in a tricuspid valve as indicated in FIGS. 8-10, a surgeon preferably uses a transcatheter venous approach, such as going down the patient's jugular vein. When a valve device of the present invention is going to be installed in a mitral valve, the surgeon can follow a transcatheter venous approach either going down the jugular vein or up from a femoral vein and then approaches the mitral valve via a transatrial puncture, i.e. through the interatrial septum, and then down through the mitral valve. In either instance, the guide shaft is fixed in the ventricular apex or ventricular wall.

Two adjustment mechanisms for adjusting the relative positions of tube 20 and guide shaft 10 are shown in FIGS. 19 and 20. With reference to FIG. 19 which is a partial view of a further embodiment, a compressible O-ring 35 is positioned around guide shaft 10 and inside tube 20. The O-ring 35 is dimensioned to form a tight fit with both the outer surface of guide shaft 10 and the inner surface of tube 20. O-ring 35 is formed of suitable material and is dimensioned so that it prevents movement of tube 20 relative to guide shaft 10 under conditions normally encountered in a heart, but can be repositioned manually or with suitable surgical instruments. In other words, ring 35 is sized to fit very snuggly on shaft 10 and will not normally move relative to shaft 10 except when ring 35 is purposely repositioned by a surgeon during surgery.

FIG. 20 illustrates a still further embodiment of an adjustment mechanism wherein guide shaft 110 is provided with a plurality of grooves 115 which partially receive a resilient O-ring 135. In this embodiment, O-ring 135 is sized to fit very snuggly within grooves 115 on shaft 110 and against the inner surface of tube 120 and will not move relative to shaft 110 or tube 120 except when ring 135 is purposely repositioned by a surgeon during surgery. The relative adjustability of the guide shaft and tube allow a surgeon to change and fine tune the position of the valve device in a patient's heart. After the valve connector has been repositioned on the guide shaft by the surgeon, there is no relative movement between the valve connector and the guide shaft unless the surgeon desires to reposition them again.

When the desired alignment is achieved, the distal end of the valve device is fixed, preferably into the ventricular apex or ventricular wall of the related ventricle via an active fixation corkscrew 12, for example, using a placement shaft 50 described above in reference to FIG. 18. Once the device is fixed in position, the guiding catheter is withdrawn leaving the anchored valve in position. This positioning of the valve occludes blood from regurgitating back into the atria.

It will be appreciated that different patients, whether human or other mammals such as dogs, have different size hearts. In order to obtain the proper positioning of the apron and valve portion, proper sealing and other functionality such as not creating undue obstruction to blood flow, different sized valve devices, for example having shafts and/or fingers of different lengths, can be utilized.

Figure 12:
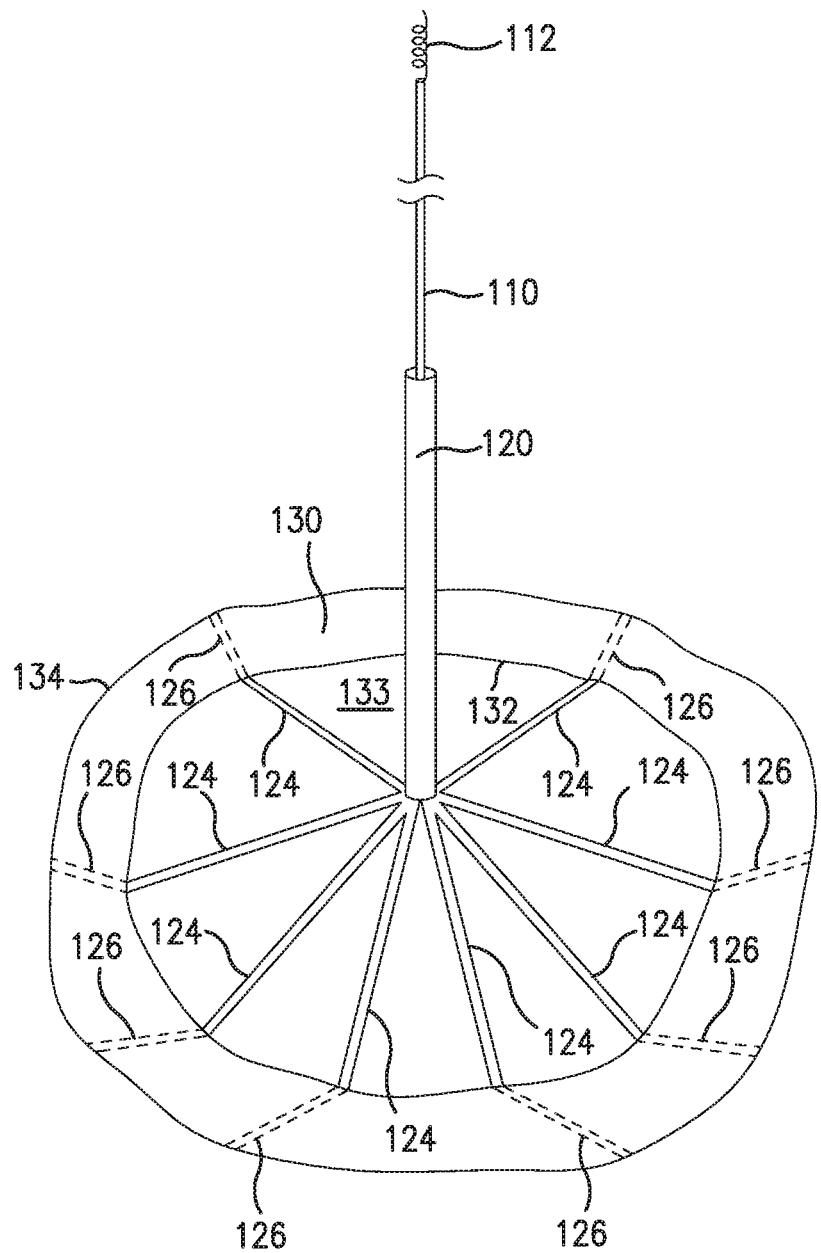
FIG. 12 is a bottom perspective view of a second embodiment of the present invention.
Figure 13:
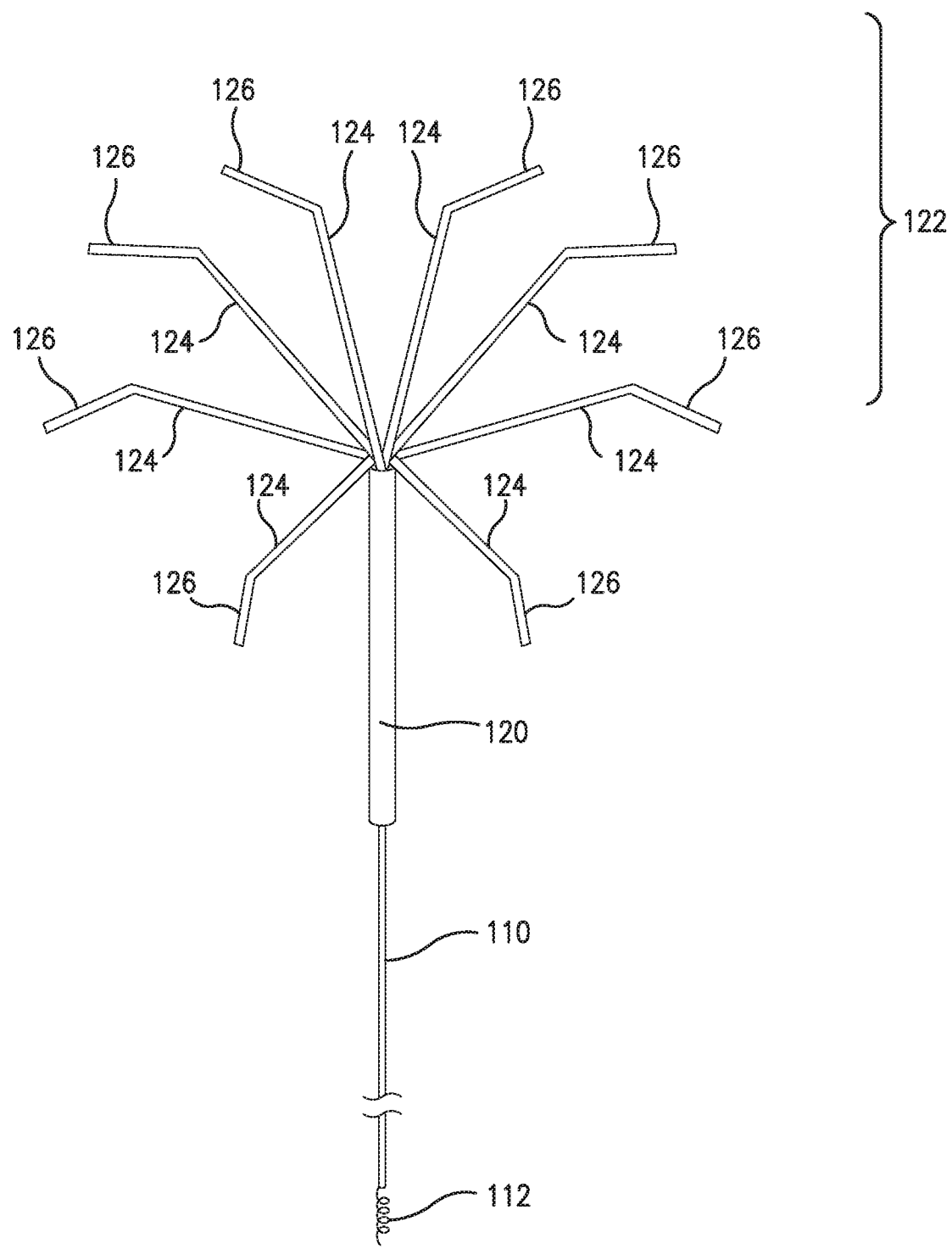
FIG. 13 is a perspective view showing the guide shaft, tube, framework and apron of the embodiment shown in FIG. 12.

FIGS. 12 and 13 illustrate another embodiment of the present invention. In this embodiment, tube 120 is formed of solid nitinol and outer portions 126 of fingers 122 are angled further downwardly, i.e. distally, than outer portion 26 shown in FIG. 6.

For purposes of illustration, FIGS. 16A-16C illustrate alternative orientations of the outer portion 26 of fingers 22 relative to inner portion 24. In FIG. 16A, outer section 26 is oriented slightly further proximally than center segment 24. In FIG. 16B outer segment 26 is generally oriented straight outwardly from the outer edge of center segment 24. In FIG. 16C, the outer segment 26 is angled slightly distally relative to the outer portion of center portion 24. With reference to angle A and angle B indicated in FIG. 16A, angle A is preferably about 90°-170°, most preferably 100°-140° while angle B is preferably about 120°-170°, most preferably about 130-170°. While other orientations are illustrated and within the scope of the present invention, the angle of an imaginary line extending from outer segment 26 to the longitudinal axis L of tube 20 is preferably less than 90°. In this manner, outer portion 26 of fingers 22 provide a greater distal force on apron 30 which is urged into contact with the native valve leaflets.

Figure 14:
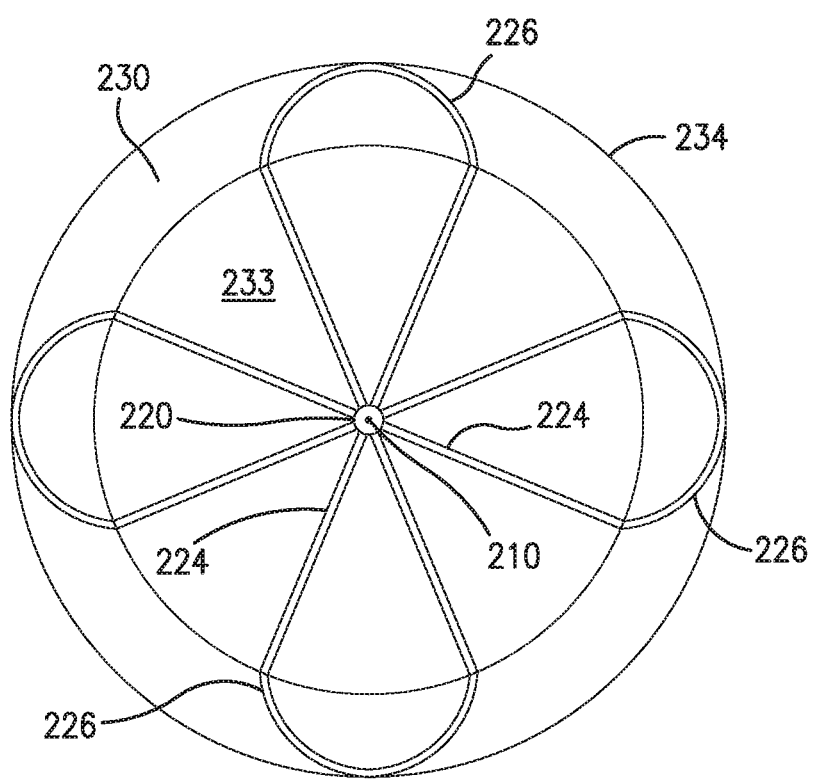
FIG. 14 is a top view of a third embodiment of the present invention showing the frame work, tube, guide shaft and apron.

FIG. 14 is a top view of another embodiment of the present invention wherein the framework comprises pairs of adjacent fingers which are joined at their outer ends to form a loop structures. In this embodiment, apron 230 is connected to outer segments 226 as described above while center sections 224 of the framework are connected to the tube 220 and prevent prolapse of an artificial valve portion (not shown). While this illustrated embodiment shows a framework with four looped structures, different numbers of loop structures can be used to form the framework.

Figure 15:
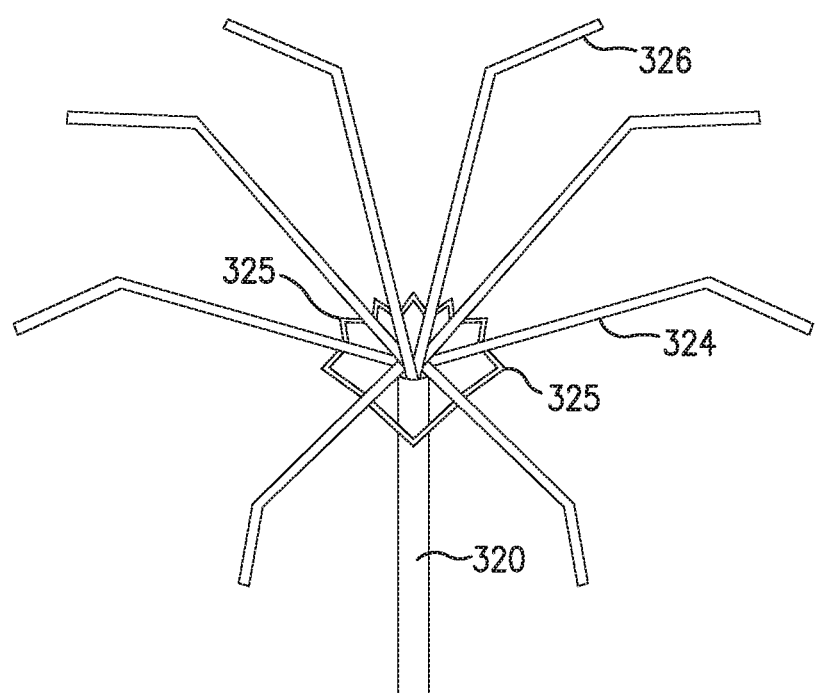
FIG. 15 is a partial, upper perspective view of the tube and framework of a fourth embodiment of the present invention.

As shown in the partial view depicted in FIG. 15, an alternative embodiment of the framework comprises additional structure 325, e.g. bridges, between the portions 324 of the fingers. Additional structure 325 provides additional protection against prolapse of the artificial valve portion. Still other embodiments not illustrated comprise additional structure on the outer portions of the fingers or on both the center and outer portions.

FIGS. 17A-17C illustrate alternative configurations for outer tips of fingers of frameworks. In order to further minimize the risk of any puncture to an atrial wall, the outer tips of the fingers which form the framework can be modified. FIG. 17A shows an outer tip which is angled further upwardly than outer portion 26 of the finger. FIG. 17B shows an outer which is gradually curved upwardly. By angling or curving the outer tips further upwardly, the tips are less likely to damage a native leaflet, an atrial wall or the atrial annulus. FIG. 17C shows an outer tip which is coiled. As used herein, the term "coiled" is used to indicate that the tip extends at least somewhat inwardly, e.g. toward the longitudinal axis of a tube if the finger is attached to a tubular valve connector. A coiled tip provides at least two advantages, namely reduces the risk of damage to native structure and provides another attachment location for the apron which can be tucked into or otherwise secured to the coil.

Figure 21:
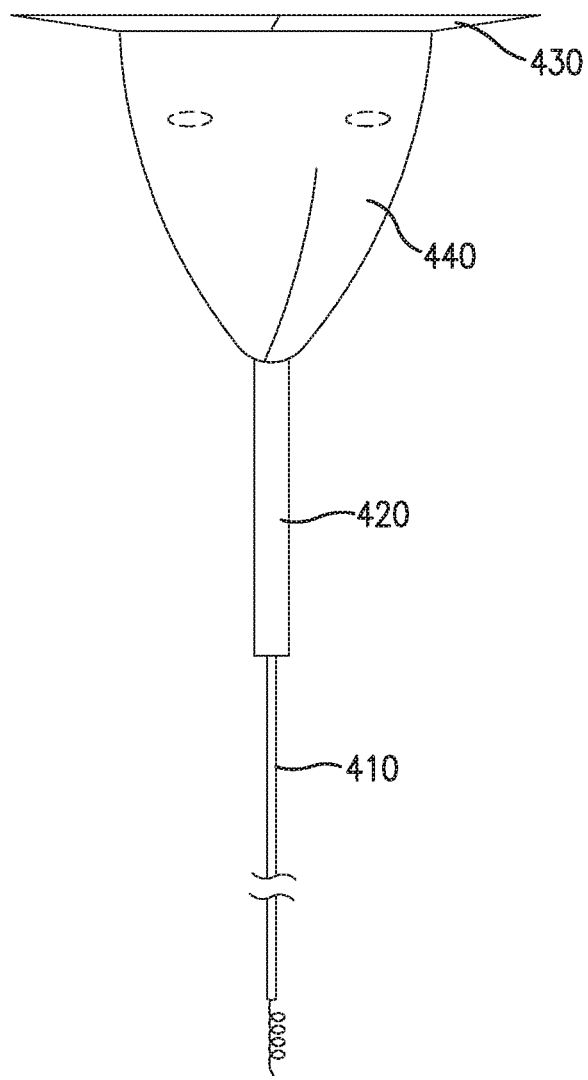
FIG. 21 is a perspective view of a fully assembled valve device of another embodiment of the present invention.

FIG. 21 illustrates a still further embodiment of an intracardiac device of the present invention. In this embodiment, the center portions of fingers (not shown) are disposed at a smaller angle to the longitudinal axis of tube 420. Similar to other embodiments, this embodiment comprises a guide shaft 410, a tube 420, valve portion 440 and apron 430.

Figure 22:
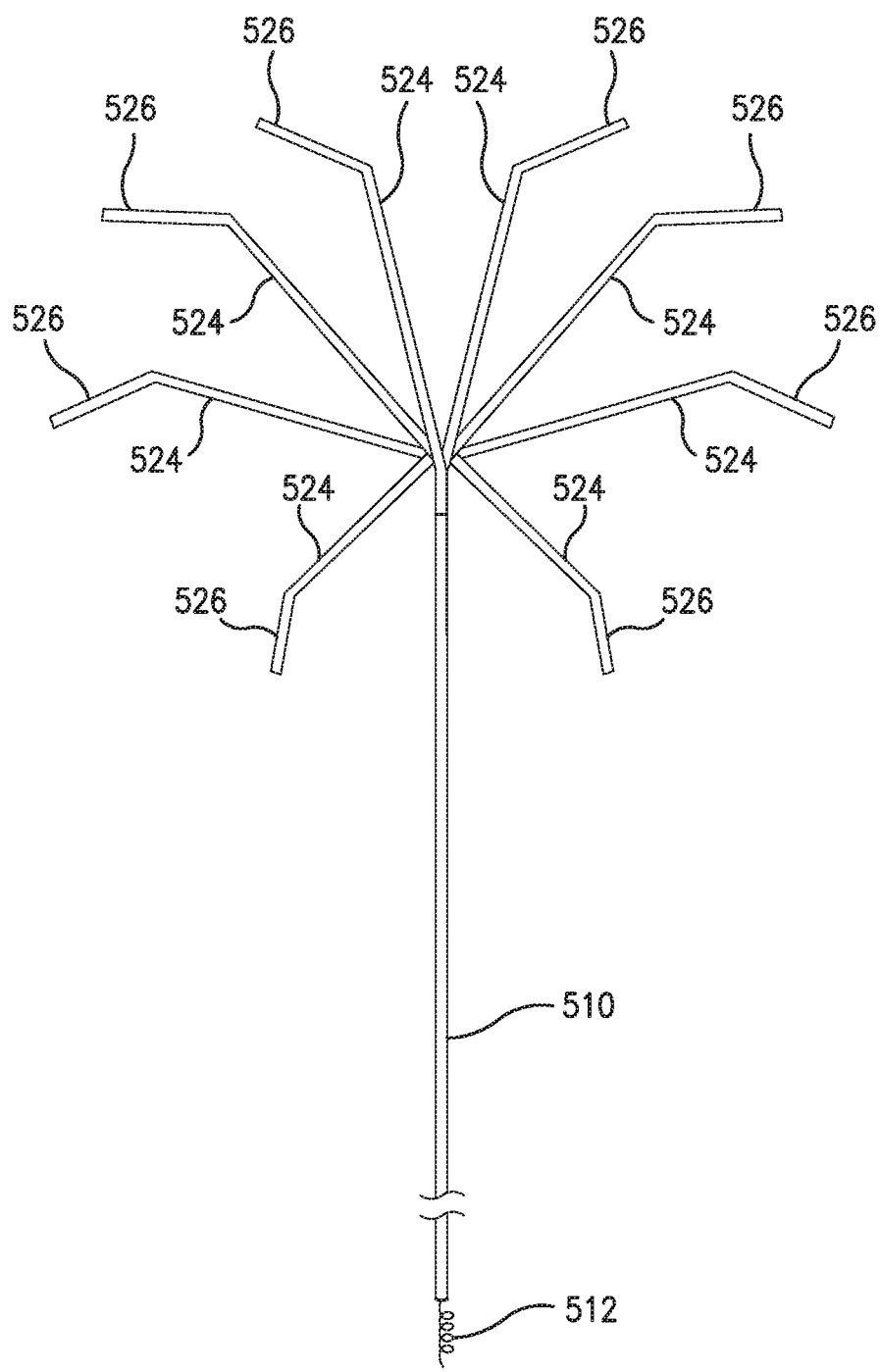
FIG. 22 is a perspective view showing the guide shaft, framework and apron of a further embodiment.

FIG. 22 is a perspective view showing the guide shaft, framework and apron of a further embodiment. In this embodiment, the framework comprising center portions 524 and outer portions 526 which support apron 530, is attached directly to the flexible guide shaft 510. This embodiment does not have the convenience of an adjustable length as in the embodiments discussed above.

One method comprises the steps of positioning one of the valve devices within a patient's heart via a transcatheter venous procedure and anchoring the device to a heart wall. The device is preferably positioned so that the valve portion is within the native leaflets, specifically with the valve portion adjacent and in contact with the native valve leaflets.

Some methods also comprise the step of adjusting the position of the tube relative to the guide shaft in order to properly position the valve portion and apron for optimal sealing and blood flow. A preferred adjustment step comprises observing the valve device while in a heart via fluoroscopy and transesophageal echocardiography, removing the heart device from the patient, adjusting the relative positions of the guide shaft and tube, and repositioning the device in the heart. In alternative methods, the position of the tube relative to the guide shaft is changed while the device is in the patient's body.

According to one method, the apron is stapled to the native atrial annulus in order to further minimize the risk of leakage of blood between the apron and the atrial annulus.

The devices and methods described above offer several advantages. The apron helps to prevent paravalvular leaks, i.e. leaks around the artificial valve. There is also no need to remove the native valves. The presence of the native leaflets contributes to the integrity of the seal during the systolic portion of the cardiac cycle.

Additionally, the framework prevents the prolapse of the native leaflets and the artificial valve portion which may also comprise leaflets. The framework extends from the valve connector to the native valve annulus. Thus, the framework is extensive in its coverage of the region in which any possible prolapse of either a native leaflet or the artificial valve portion could occur.

The invention claimed is:

1. A method of deploying a heart valve implant in a patient comprising the steps of:
  providing a heart valve implant comprising:
    a guide shaft comprising a distal end and a proximal end;
    an anchor coupled to said guide shaft proximate said distal end;
    a valve connector connected to said guide shaft;
    a framework connected to valve connector and extending radially outwardly from said valve connector;
    said framework comprising a first portion extending radially outwardly from said valve connector and a second portion extending further radially outwardly from said first portion of said framework;
    a valve portion connected to said framework and disposed proximate to and distally of said first portion of said framework, at least a portion of said valve portion is movable away from said framework during diastole and into contact with said framework during systole; and
    an apron connected to said framework and disposed proximate to and distally of said second portion of said framework, said apron comprising material which permits ingrowth of native heart tissue;
  positioning said heart valve implant at least partially within a heart via a transcatheter venous procedure; and
  securing said anchor to native heart tissue.

2. A method of deploying a heart valve implant in a patient according to claim 1 further comprising the step of adjusting the position of the valve portion relative to said guide shaft.

3. A method of deploying a heart valve implant in a patient according to claim 2 wherein said adjusting step comprises changing the position of said valve portion relative to said guide shaft.

4. A method according to claim 1 further comprising the step of positioning said valve portion in contact with native heart leaflets.

5. A method according to claim 1 further comprising the step of positioning said valve portion adjacent said native heart leaflets.

6. A method according to claim 1 further comprising the step of positioning said valve portion within with native heart leaflets.

7. A method according to claim 1 further comprising the step of stapling said apron to the native atrial annulus.

8. A method according to claim 1 further comprising the step of affixing said apron to the native atrial annulus.

9. A method of deploying a heart valve implant in a patient comprising the steps of:
  providing a heart valve implant comprising:
    a guide shaft comprising a distal end and a proximal end;
    an anchor coupled to said guide shaft proximate said distal end;
    a valve connector connected to said guide shaft;
    a framework connected to valve connector and extending radially outwardly from said valve connector;
    said framework comprising a first portion extending radially outwardly from said valve connector and a second portion extending further radially outwardly from said first portion of said framework;
    a valve portion connected to said framework and disposed proximate to and distally of said first portion of said framework, at least a portion of said valve portion is movable away from said framework during diastole and into contact with said framework during systole; and
    an apron connected to said framework and disposed proximate to and distally of said second portion of said framework, said apron comprising material which permits ingrowth of native heart tissue;
  positioning said heart valve implant at least partially within a heart via a transcatheter procedure; and
  securing said anchor to native heart tissue.

10. A method of deploying a heart valve implant in a patient according to claim 9 further comprising the step of adjusting the position of the valve portion relative to said guide shaft.

11. A method of deploying a heart valve implant in a patient according to claim 10 wherein said adjusting step comprises changing the position of said valve portion relative to said guide shaft.

12. A method according to claim 9 further comprising the step of positioning said valve portion in contact with native heart leaflets.

13. A method according to claim 9 further comprising the step of positioning said valve portion adjacent said native heart leaflets.

14. A method according to claim 9 further comprising the step of positioning said valve portion within with native heart leaflets.

15. A method according to claim 9 further comprising the step of affixing said apron to the native atrial annulus.

16. A method according to claim 15 further comprising the step of stapling said apron to the native atrial annulus.

* * * * *